United States Patent
Lytinas

(10) Patent No.: US 9,301,781 B2
(45) Date of Patent: Apr. 5, 2016

(54) BONE REGENERATION DEVICE FOR BONES, AND METHOD OF USE

(75) Inventor: Michael Lytinas, Boston, MA (US)

(73) Assignee: XCI Licensing, Inc., San Antonio, TX (US)

( * ) Notice: Subject to any disclaimer, the term of this patent is extended or adjusted under 35 U.S.C. 154(b) by 104 days.

(21) Appl. No.: 13/352,897

(22) Filed: Jan. 18, 2012

(65) Prior Publication Data

US 2012/0116469 A1    May 10, 2012

Related U.S. Application Data

(63) Continuation of application No. 11/643,390, filed on Dec. 21, 2006, now Pat. No. 8,109,932, which is a continuation of application No. 10/410,610, filed on Apr. 10, 2003, now Pat. No. 7,169,151.

(51) Int. Cl.
*A61B 17/56* (2006.01)
*A61B 17/58* (2006.01)
*A61B 17/88* (2006.01)

(52) U.S. Cl.
CPC ............... *A61B 17/56* (2013.01); *A61B 17/58* (2013.01); *A61B 17/88* (2013.01)

(58) Field of Classification Search
CPC ................................ A61B 17/56; A61B 17/58
USPC ........................................... 606/86 R, 53, 60
See application file for complete search history.

(56) References Cited

U.S. PATENT DOCUMENTS

| | | | |
|---|---|---|---|
| 59,388 A | * | 11/1866 | Hadfield .............. A61H 9/005 4/535 |
| 1,355,846 A | | 10/1920 | Rannells |
| 1,629,108 A | * | 5/1927 | Lake ..................... A61F 5/34 601/151 |
| 2,547,758 A | | 4/1951 | Keeling |
| 2,632,443 A | | 3/1953 | Lesher |
| 2,682,873 A | | 7/1954 | Evans et al. |
| 2,910,763 A | | 11/1959 | Lauterbach |
| 2,969,057 A | | 1/1961 | Simmons |
| 3,066,672 A | | 12/1962 | Crosby, Jr. et al. |
| 3,367,332 A | | 2/1968 | Groves |

(Continued)

FOREIGN PATENT DOCUMENTS

| AU | 550575 A1 | 8/1982 |
|---|---|---|
| AU | 745271 | 4/1999 |

(Continued)

OTHER PUBLICATIONS

N. A. Bagautdinov, "Variant of External Vacuum Aspiration in the Treatment of Purulent Diseases of the Soft Tissues," *Current Problems in Modem Clinical Surgery: Interdepartmental Collection*, edited by V. Ye Volkov et al. (Chuvashia State University, Cheboksa, U.S.S.R. 1986); pp. 94-96 (copy and certified translation).

(Continued)

*Primary Examiner* — Christian Sevilla

(57) ABSTRACT

A method of stimulating bone regeneration in a discontinuous section of a long bone in a subject requiring same, comprising the step of applying to said discontinuous section of the bone an effective vacuum for an effective length of time. A device for carrying out the method consisting of a sealable tubular-shaped sleeve or cuff that fits snugly and sealably around the bone section to be treated and that can be evacuated via a port that is integral to the sleeve or port.

18 Claims, 1 Drawing Sheet

(56) References Cited

U.S. PATENT DOCUMENTS

| | | | |
|---|---|---|---|
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 3,859,989 A * | 1/1975 | Spielberg | A61H 9/005 601/11 |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,520 A * | 6/1993 | Shroot | A61M 35/00 604/20 |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,568,788 A * | 10/1996 | van den Berg | A01J 5/0133 119/14.02 |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,117,111 A * | 9/2000 | Fleischmann | 604/180 |
| 6,135,116 A * | 10/2000 | Vogel | A61F 13/069 128/898 |
| 6,143,035 A * | 11/2000 | McDowell | 623/22.11 |
| 6,167,838 B1 * | 1/2001 | van den Berg | A01J 5/007 119/14.02 |
| 6,241,747 B1 | 6/2001 | Ruff | |
| 6,287,316 B1 | 9/2001 | Agarwal et al. | |
| 6,293,917 B1 * | 9/2001 | Augustine et al. | 602/2 |
| 6,345,623 B1 | 2/2002 | Heaton et al. | |
| 6,458,109 B1 * | 10/2002 | Henley et al. | 604/304 |
| 6,488,643 B1 | 12/2002 | Tumey et al. | |
| 6,491,693 B1 * | 12/2002 | Lytinas | A61B 17/88 606/123 |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,169,151 B1 * | 1/2007 | Lytinas | A61B 17/88 606/86 R |
| 7,214,202 B1 * | 5/2007 | Vogel | A61F 13/069 601/11 |
| 7,998,125 B2 * | 8/2011 | Weston | A61M 1/008 52/2.18 |
| 8,663,198 B2 * | 3/2014 | Buan | A61F 13/02 604/305 |
| 2002/0077661 A1 | 6/2002 | Saadat | |
| 2002/0115951 A1 | 8/2002 | Norstrem et al. | |
| 2002/0115952 A1 * | 8/2002 | Johnson et al. | 602/41 |
| 2002/0120185 A1 | 8/2002 | Johnson | |
| 2002/0143286 A1 | 10/2002 | Tumey | |
| 2002/0198504 A1 * | 12/2002 | Risk et al. | 604/318 |
| 2003/0040687 A1 * | 2/2003 | Boynton et al. | 601/6 |
| 2004/0039391 A1 * | 2/2004 | Argenta | A61F 5/34 606/86 R |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |

(56) References Cited

FOREIGN PATENT DOCUMENTS

| | | |
|---|---|---|
| WO | WO 97/18007 | 5/1997 |
| WO | WO 99/13793 | 3/1999 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainase"; Contemporary Surgery, vol. 34, Jun. 1989, pp. 59-63.

Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosuface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinović, V. Ð ukić, Ž. Maksimović, D. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).

* cited by examiner

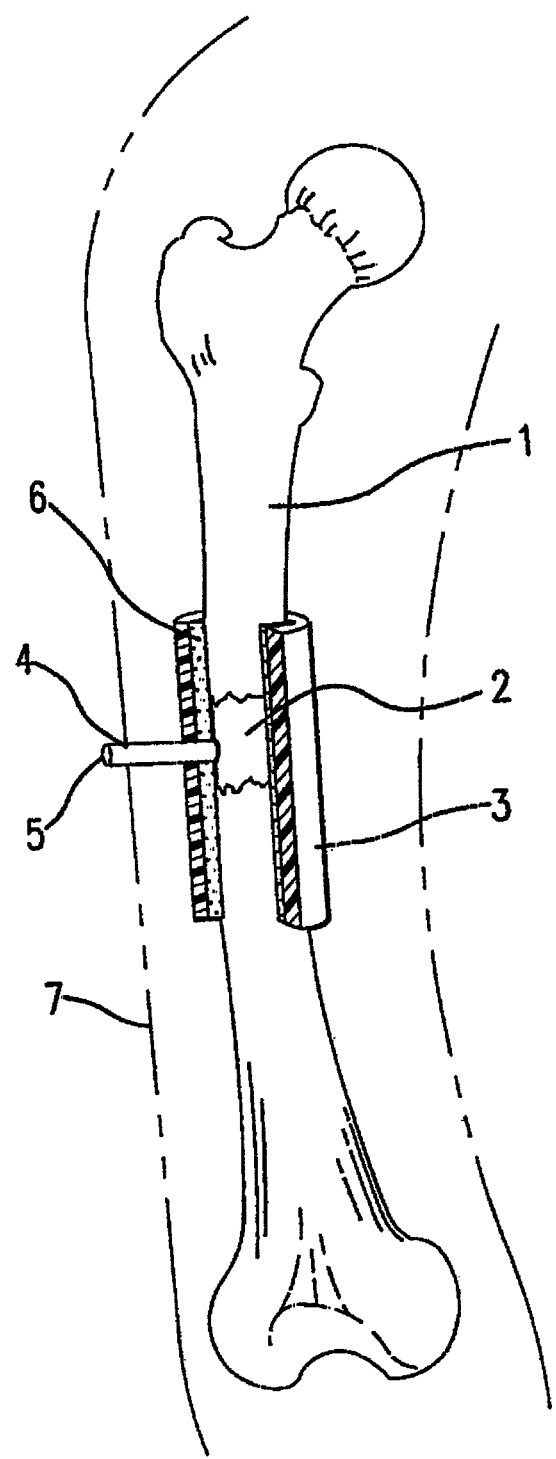

BONE REGENERATION DEVICE FOR BONES, AND METHOD OF USE

CROSS-REFERENCE TO RELATED APPLICATIONS

This application is a continuation of U.S. patent application Ser. No. 11/643,390, filed Dec. 21, 2006, now U.S. Pat. No. 8,109,932 which is a continuation of U.S. patent application Ser. No. 10/410,610, filed Apr. 10, 2003, now U.S. Pat. No. 7,169,151, both of which are hereby incorporated by reference.

BACKGROUND OF THE INVENTION

1. Field of the Invention

The invention is concerned with local bone regeneration for long bones. More specifically, the invention relates to the use of locally-applied vacuum to stimulate osteoblastic activity in long bones with discontinuity defects.

2. Description of Related Art

Osteogenesis, the growth of new bone, is a part of the normal healing process, and involves recruiting and activating osteoblast cells in the bone. This can be a slow process, particularly in the elderly and after severe trauma to the bone and after disease. The ability to accelerate osteogenesis would speed the healing process after trauma and after orthopedic and dental procedures. Methods to accelerate the process, particularly in local areas of bone, have been a holy grail for scientists for many years.

Current techniques of bone regeneration include: traditional methods such as distraction osteogenesis in which bone is pulled in an appropriate direction to stimulate growth, and bone grafting; and, experimental techniques that include use of drugs such as OP-1 that stimulate osteoblasts, implanting biomaterials laced with molecular signals designed to trigger the body's own repair mechanism, injecting bone marrow stem cells into the affected areas, and, transfusing cells that carry genes that code for bone-repair proteins. None of these methods are totally satisfactory, for a host of reasons. For a review of this subject see: Service, Science, 289:1498 (2000).

Distraction osteogenesis requires a bulky device and requires a very long period before positive results are seen. Bone grafting is limited by the quantity and quality of the patient's bone available for grafting. Biocompatible polymeric matrices without or with natural or recombinant bone morphogenic proteins suffer from a need for a very large and very expensive quantities of these signal proteins. The gene therapy procedure suffers from the general problems of gene therapy in general. The use of the stem cell approach is greatly limited by the scarcity and expense of such cells; for example, in 50-year olds, there is only one stem cell in 400,000 bone marrow cells. (see Service, 2000, above.)

Applicant has previously described a device that applies subatmospheric pressures to a fractured or lesioned area of a flat bone (e.g., scapula), and thereby promotes osteogenesis and consequent bone healing in such areas (Lytinas, U.S. Pat. No. 6,491,693, which is incorporated herein by reference). However, for anatomical reasons such a device is not suitable for non-flat long bones of the upper and lower extremities, particularly where blunt trauma from accidents and/or projectiles produces in the long bone discontinuous defects leaving gaps of 2.5 cm and more. In the past such discontinuous defects have been treated orthopedically by grafting into the discontinuity pieces of the bone taken from elsewhere in the body. More often than not, such grafting does not completely fill the discontinuity, thereby leading to poor healing (fibrous displacement) and shortened extremities.

Clearly, there is an acute need for a safe, simple, rapid, inexpensive and efficient device and method for producing osteogenesis in discontinuous regions of long bones. Such a device and method, based in principal on the vacuum technique discovered by the applicant (U.S. Pat. No. 6,491,693) has now been discovered, and is described below.

SUMMARY

A device and method for producing bone regeneration (osteogenesis) in a discontinuous local section of a long bone in a subject requiring same, comprising the step of applying to the local section of the bone a vacuum (subatmospheric pressure) for an effective period of time.

In one embodiment, the discontinuous section of the long bone is sealed from the atmosphere with a flexible, sterilizable sleeve or cuff device of a dimension and curvature suitable to enclose and fit sealably tightly over the discontinuous or fractured section of the long bone, the device being connected through a sealable exit port to a source of vacuum, such that the discontinuous section of the long bone can be evacuated for an appropriate length of time.

BRIEF DESCRIPTION OF THE DRAWINGS

FIG. 1 is a sketch of the sleeve/cuff device of the invention.

DETAILED DESCRIPTION OF THE ILLUSTRATIVE EMBODIMENTS

The essence of the invention is the production of bone regeneration (osteoblastic cell-induced osteogenesis) in a desired section of a long bone by the application to this section a vacuum (within the context of this specification the term vacuum is to be considered synonymous with subatmospheric pressure) for an effective length of time.

The method can be applied to any long bone in humans or animals. It can be applied to a wide variety of medical conditions, e.g., a bone that has been shattered by such trauma that produces a discontinuous section that requires osteogenesis; a bone that requires lengthening; a bone that needs reshaping, as after an accident; a bone after surgical removal of a cancerous or cystic section of the bone; and, in bone resorption areas (alveolar region).

The device of the invention is suitable for a variety of long bones, including a femur, a clavicle, ribs, humerus, ulna and radius, carpal and metacarpal bones and their phalanges, tibia, fibula, and, tarsal and metatarsal bones and their phalanges, among others.

At the heart of the invention is a device that produces the vacuum on the discontinuous or fractured section of the long bone. A highly preferred device is an evacuatable sleeve or cuff (the two terms are used interchangeably) that can be fitted around the discontinuous section or fracture of the bone and that can be maintained under vacuum through a port. The evacuation port is continuous with both the interior of the sleeve or cuff and the skin surrounding the bone being treated so that repeated re-evacuations may be easily applied by medical personnel.

In FIG. 1, 1 is a representative example of a long bone being treated; 2 is a representative discontinuity defect; 3 is the sleeve or cuff that encloses the bone both above and below the discontinuity; 4 is the vacuum port that extends from the interior of the sleeve or cuff to the outside the skin; 5 is the sealable port orifice that is connected to a vacuum pump or the like; 6 depicts sealant that is placed between the sleeve or cuff and the bone, above and below the discontinuity; and 7 is the skin.

The sleeve or cuff should be composed of flexible, sterilizable (e.g., autoclavable) material. It may be made of a light biocompatible metal or plastic, and its walls should be sufficiently thick so as not to collapse under vacuum. Snugness of the sleeve or cuff device is accomplished, in part, by fabricating the device so that the curvature of the portion resting against the bone is designed to fit the particular bone being treated, and, in part, by the flexibility of the sleeve or cuff. Sleeves or cuffs with a wide variety of sizes and shapes may be fabricated by well-known methods and kept on hand under sterile conditions.

The sleeve or cuff of the inventive device is hermetically glued to the bone above and below the discontinuity section with any appropriate surgical glue, e.g., an elastic silicone Nexaband Liquid, VPL, Inc. without or with glues of the type of KRAZY GLUE. It is important that the sleeve or cuff have elastic properties so that the vacuum seal will not be broken if the bone moves in place.

The sleeve or cuff, once attached to the bone, is evacuated by a vacuum pump (e.g. Nalgene vacuum pump, although any other vacuum pump is suitable) by means of the port (4 and 5 in FIG. 1). Following attainment of the desired degree of vacuum, the connection between the device and the pump is sealed. As the port extends through the skin, it is readily accessible for repeated evacuations of the system. The degree of vacuum is determined by the extent of the discontinuity. For example, as little as 30 in. Hg is sufficient to induce bone regeneration in a skeletal bone. The vacuum port may also be fitted with an attached vacuum measuring gauge.

The device is maintained in place for an appropriate length of time before being removed. Determination of this appropriate length of time is based on the clinical condition being treated and the degree of regeneration required. This determination does not require undue experimentation by the medical or dental surgeon applying the technique.

The progress of bone regeneration may be followed radiographically, as a plastic version of the inventive device is radiolucent and the new bone is not. The osteoid precursor stage of bone regeneration may not, however, always be visible by X-ray. At an appropriate time, the inventive device may be removed surgically, preferably by cutting it away from the bone by, for example, a dental burr.

The following example merely provides an embodiment of the inventive method, and should not be construed as limiting the claims in any way.

EXAMPLE 1

The Surgical Protocol

Under sterile conditions, the bone to be treated is reached surgically. Skin, fat, muscles, etc. are blunt-resected from the bone.

The autoclaved sleeve or cuff device is slipped around the desired discontinuity section of the bone, and sealed to the bone with surgical glue (e.g. Nexaband liquid, Veterinary Products Laboratories, Inc.).

The vacuum port of the device is attached to a vacuum pump, and the device evacuated to the desired pressure, e.g. about 30 in. Hg. At this point the vacuum port is sealed so as to maintain the vacuum. The subcutaneous tissues are closed with sutures, e.g., a 4-0 Dexonsuture, and the skin sutured closed.

The degree of vacuum can be monitored by a vacuum gauge attached to the vacuum port.

At an appropriate length of time, e.g., about four weeks, the device (still well-sealed) is removed from the long bone. A bone augmentation at the site of the treatment will be noted.

I claim:

1. A device for stimulating osteoblastic activity in a discontinuous section of a long bone, the device comprising:
   a sleeve or cuff configured to enclose a portion of the long bone above and below the discontinuous section, and adapted to enclose a circumference of the long bone above and below the discontinuous section;
   a sealable port in fluid communication with an interior of the sleeve or cuff, the sealable port adapted to transmit a vacuum pressure to the discontinuous section of the long bone; and
   wherein the sleeve or cuff is adapted to resist collapse under the vacuum pressure.

2. The device according to claim 1, wherein the discontinuous section of the long bone is at least 2.5 cm.

3. The device according to claim 1, wherein the sleeve or cuff resists collapse under the vacuum pressure by being sufficiently thick.

4. The device according to claim 1, wherein the sleeve or cuff comprises a dimension and curvature fabricated to fit snugly around the discontinuous section of the long bone, and wherein the sleeve or cuff is composed of an evacuatable, sterilizable, flexible, sealable material.

5. The device according to claim 4, wherein the dimension and curvature of the sleeve or cuff is predetermined based on which type of long bone is being treated, and wherein the long bone is selected from a group comprising a femur, a clavicle, ribs, humerus, ulna, and radius, carpal and metacarpal bones and their phalanges, tibia, fibula, and tarsal and metatarsal bones and their phalanges.

6. The device according to claim 1, wherein the sleeve or cuff is a biocompatible metal.

7. The device according to claim 1, wherein the sleeve or cuff is a biocompatible plastic.

8. The device according to claim 1, wherein:
   an elastic seal comprises a glue; and
   the glue has elastic properties to maintain the elastic seal at the discontinuous section of the long bone to resist breakage of the elastic seal if the section of bone above the discontinuous section moves relative to the section of bone below the discontinuous section.

9. The device according to claim 1, wherein the vacuum pressure is monitored by a pressure gauge attached to the sealable port.

10. A system for stimulating new bone formation in a long bone with a discontinuity defect, the system comprising:
    a sleeve or cuff configured to enclose the long bone above and below the discontinuity defect, and adapted to enclose a circumference of the long bone above and below the discontinuity defect;
    a sealable port in fluid communication with an interior of the sleeve or cuff; and
    a vacuum pump fluidly connected to the sealable port for supplying a vacuum pressure to the sealable port and the discontinuity defect.

11. The system according to claim 10, wherein the sealable port extends from the interior of the sleeve or cuff through skin to an exterior of a body, the sealable port adapted to transmit the vacuum pressure to the discontinuity defect in the long bone.

12. The system according to claim 10, wherein the sleeve or cuff is adapted to resist collapse under the vacuum pressure.

13. The system according to claim 10, wherein the sleeve or cuff is composed of an evacuatable, sterilizable, flexible, sealable material.

14. The system according to claim 13, wherein a dimension and curvature of the sleeve or cuff is predetermined based on a type of the long bone, and wherein the type of the long bone is selected from a group comprising a femur, a clavicle, ribs, humerus, ulna, and radius, carpal and metacarpal bones and their phalanges, tibia, fibula, and tarsal and metatarsal bones and their phalanges.

15. The system according to claim 10, wherein the sleeve or cuff is a biocompatible metal.

16. The system according to claim 10, wherein the sleeve or cuff is a biocompatible plastic.

17. The system according to claim 10, further comprising:
- an elastic seal configured to hermetically glue the sleeve or cuff to the long bone above and below the discontinuity defect; and
- wherein the elastic seal is configured to resist breakage if the long bone above the discontinuity defect moves relative to the long bone below the discontinuity defect.

18. The system according to claim 10, wherein the vacuum pressure is monitored by a pressure gauge attached to the sealable port.

* * * * *

UNITED STATES PATENT AND TRADEMARK OFFICE
CERTIFICATE OF CORRECTION

PATENT NO.       : 9,301,781 B2
APPLICATION NO.  : 13/352897
DATED            : April 5, 2016
INVENTOR(S)      : Michael Lytinas It is certified that error appears in the above-identified patent and that said Letters Patent is hereby corrected as shown below:

In title page, item (73) Assignee is incorrectly spelled. The correct spelling is KCI Licensing, Inc., San Antonio, TX (US)

Signed and Sealed this
Twenty-third Day of August, 2016

Michelle K. Lee
*Director of the United States Patent and Trademark Office*